United States Patent
Schimperna et al.

(10) Patent No.: US 11,930,705 B2
(45) Date of Patent: Mar. 12, 2024

(54) DIARYLOXYBENZOHETERODIAZOLE COMPOUNDS DI-SUBSTITUTED WITH THIENOTHIOPHENIC GROUPS

(71) Applicant: ENI S.P.A., Rome (IT)

(72) Inventors: Giuliana Schimperna, Novara (IT); Luigi Abbondanza, Novara (IT); Antonio Alfonso Proto, Novara (IT); Stefano Zanardi, Novara (IT)

(73) Assignee: ENI S.P.A., Rome (IT)

( * ) Notice: Subject to any disclaimer, the term of this patent is extended or adjusted under 35 U.S.C. 154(b) by 107 days.

(21) Appl. No.: 17/775,900

(22) PCT Filed: Nov. 12, 2020

(86) PCT No.: PCT/IB2020/060661
§ 371 (c)(1),
(2) Date: May 11, 2022

(87) PCT Pub. No.: WO2021/094976
PCT Pub. Date: May 20, 2021

(65) Prior Publication Data
US 2022/0399509 A1    Dec. 15, 2022

(30) Foreign Application Priority Data
Nov. 12, 2019  (IT) .......................... 102019000020970

(51) Int. Cl.
*H10K 85/60*     (2023.01)
*C07D 495/04*    (2006.01)
*H10K 30/87*     (2023.01)

(52) U.S. Cl.
CPC ....... *H10K 85/6576* (2023.02); *C07D 495/04* (2013.01); *H10K 30/87* (2023.02); *H10K 85/657* (2023.02)

(58) Field of Classification Search
CPC .. H10K 30/87; H10K 30/657; H10K 30/6576; C07D 495/04
See application file for complete search history.

(56) References Cited

U.S. PATENT DOCUMENTS 7,223,484 B2 *  5/2007  Stossel ................ C07D 513/04
                                                   548/134
2006/0052612 A1 *  3/2006  Stossel ................ C07D 285/14
                                                   548/134

(Continued)

FOREIGN PATENT DOCUMENTS

CN    104098758 A    10/2014
WO       2019132 A1   7/2019

OTHER PUBLICATIONS

International Search Report dated Jan. 13, 2021 for PCT Appl. No. PCT/IB2020/059769.

(Continued)

*Primary Examiner* — Golam Mowla
(74) *Attorney, Agent, or Firm* — Ruggiero McAllister McMahon LLC

(57) ABSTRACT

There is a diaryloxybenzoheterodiazole compound di-substituted with thienothiophenic groups having general formula (Ia):

(Continued)

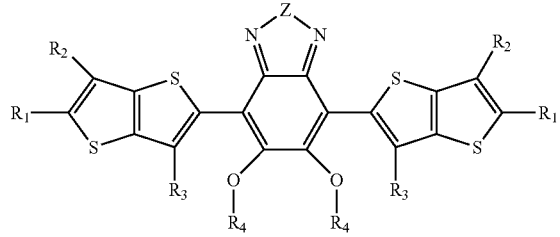

(Ia)

The diaryloxybenzoheterodiazole compound di-substituted with thienothiophenic groups having general formula (Ia) can be advantageously used as a spectrum converter in luminescent solar concentrators (LSCS) capable, in turn, of improving the performance of photovoltaic devices (or solar devices), selected for example, between photovoltaic cells (or solar cells), photovoltaic modules (or solar modules), either on a rigid support, or on a flexible support. More particularly, said photovoltaic devices (or solar devices) can be advantageously used in the construction of greenhouses.

12 Claims, 2 Drawing Sheets

(56) References Cited

U.S. PATENT DOCUMENTS

| | | | |
|---|---|---|---|
| 2008/0093985 A1* | 4/2008 | Morishita | H10K 85/611 |
| | | | 257/E51.026 |
| 2015/0291575 A1* | 10/2015 | Santarelli | C07D 285/14 |
| | | | 548/126 |

OTHER PUBLICATIONS

Written Opinion Report dated Jan. 13, 2021 for PCT Appl. No. PCT/IB2020/059769.

Goeker et al; "The Effect of the Different Donor Units on Flourescent Conjugated Polymers Containing 2,1,3-benzooxadiazole as the Acceptor Unit"; Journal of Electroanalytical Chemistry; May 22, 2015; pp. 80-89.

* cited by examiner

DIARYLOXYBENZOHETERODIAZOLE COMPOUNDS DI-SUBSTITUTED WITH THIENOTHIOPHENIC GROUPS

CROSS-REFERENCE TO RELATED APPLICATIONS

This patent APPLICATION claims priority from PCT Application No. PCT/IB2020/060661, filed Nov. 12, 2020, which claims priority based on Italian Patent Application No. 102019000020970 filed on Nov. 12, 2019, the entire disclosures of which are incorporated herein by reference.

FIELD OF THE DISCLOSURE

The present disclosure relates to a diaryloxybenzoheterodiazole compound di-substituted with thienothiophenic groups.

More particularly, the present disclosure relates to diaryloxybenzoheterodiazole compound di-substituted with thienothiophenic groups having the specific general formula (Ia) below.

The present disclosure also relates to a luminescent solar concentrator (LSC) including at least one diaryloxybenzoheterodiazole compound di-substituted with thienothiophenic groups, as well as a photovoltaic device (or solar device) comprising said luminescent solar concentrators (LSC).

The present disclosure also relates to the use of said photovoltaic devices (or solar devices) in the construction of greenhouses.

DESCRIPTION OF THE RELATED ART

In the state of the art, one of the main limits to the exploitation of solar radiation energy is represented by the capability of photovoltaic devices (or solar devices) to optimally absorb only the radiations having wavelengths that fall within a narrow spectral range.

With a spectral range of solar radiation extending from wavelengths of about 300 nm to wavelengths of about 2500 nm, photovoltaic cells (or solar cells) based on crystalline silicon have for example an optimal absorption spectrum (effective spectrum) in the range 900 nm-1100 nm, while polymeric photovoltaic cells (or solar cells) are liable to damage if exposed to radiations with wavelengths lower than about 500 nm, due to phenomena of induced photo-degradation which become significant below this limit. Typically, the efficiency of the photovoltaic devices (or solar devices) of the state of the art is maximum in the region of the spectrum between 570 nm and 680 nm (yellow-orange).

The aforementioned drawbacks lead to a limited external quantum efficiency (EQE) of the photovoltaic devices (or solar devices), defined as the ratio between the number of electron-hole pairs generated in the semiconductor material being part of the photovoltaic devices (or solar devices) and the number of photons incident on said photovoltaic devices (or solar devices).

To improve the external quantum efficiency (EQE) of photovoltaic devices (or solar devices) instruments have been developed that, interposed between the source of light radiation (the sun) and photovoltaic devices (or solar devices), selectively absorb incident radiation having wavelengths outside the effective spectrum of said photovoltaic devices (or solar devices), emitting the absorbed energy in the form of photons of wavelength included in the effective spectrum. Said instruments correspond to luminescent solar concentrators (LSCs). When the energy of the photons that are re-emitted by the luminescent solar concentrators (LSCs) is higher than that of the incident photons, the photoluminescence process, including the absorption of solar radiation and the subsequent re-emission of photons at a shorter wavelength, is also called up-conversion process. Conversely, when the energy of the photons that are emitted by luminescent solar concentrators (LSCs) is lower than that of the incident photons, the photoluminescence process is called "down-conversion" process (or "down-shifting").

Generally, said luminescent solar concentrators (LSCs) consist of large plates of a material transparent to solar radiation (for example, polymeric or inorganic glasses), wherein fluorescent compounds, acting as spectrum converters, are dispersed or chemically linked to said material. Due to the optical phenomenon of total reflection, the radiation emitted by the fluorescent compounds is "guided" towards the thin edges of the plate where it is concentrated on photovoltaic cells (or solar cells) placed therein. In this way, large surfaces of low-cost materials (photoluminescent plates) can be used to concentrate light on small surfaces of high-cost materials [photovoltaic cells (or solar cells)].

The fluorescent compounds can be deposited on the glass support in the form of a thin film or, as in the case of polymeric materials, they can be dispersed inside the polymeric matrix. Alternatively, the polymeric matrix can be directly functionalized with fluorescent chromophores groups.

Ideally, to be used in spectrum converters, fluorescent compounds must have the following characteristics:
high luminescence quantum efficiency ($\Phi$) [($\Phi$) being defined according to the equation below (1) as the ratio between the number of photons emitted and the number of photons absorbed by a luminescent molecule per unit of time and has a maximum value equal to 1]:
($\Phi$)=number of emitted photons/number of absorbed photons (1);
broad absorption band in the spectral region wherein the photovoltaic device (or solar device) is poorly efficient;
high molar extinction coefficient ($\varepsilon$);
narrow emission band in the spectral region wherein the photovoltaic device (or solar device) is more efficient;
well separated absorption and emission bands to avoid or minimize self-absorption phenomena.

It is known that some benzothiadiazole compounds, in particular 4,7-di-(thien-2'-yl)-2,1,3-benzothiadiazole (DTB), are fluorescent compounds usable in the construction of luminescent solar concentrators (LSCs). Compounds of this type have been described, for example, in the international patent application WO 2011/048458 in the name of the Applicant.

4,7-di-(thien-2'-yl)-2,1,3-benzothiadiazole (DTB) is characterized by an emission centred around 579 nm, a value which corresponds to an energy well above the minimum threshold of operative photovoltaic cells (or solar cells), which threshold, for example, corresponds to a wavelength of about 1100 nm for the most common silicon-based photovoltaic cells (or solar cells). Moreover, its absorption of the light radiation is intense and extended over a relatively broad range of wavelengths, ranging indicatively from 550 nm (the wavelength of the green radiation) to the ultraviolet radiations. Finally, 4,7-di-(thien-2'-yl)-2,1,3-benzothiadiazole (DTB) has a Stokes shift, in dichloromethane solution ($CH_2Cl_2$), equal to 134 nm, much higher than those of most of the commercial products so far proposed for use in luminescent solar concentrators (LSCs).

For these reasons, the use of 4,7-di-(thien-2'-yl)-2,1,3-benzothiadiazole (DTB) has made it possible to create luminescent solar concentrators (LSCs) of excellent quality.

However, 4,7-di-(thien-2'-yl)-2,1,3-benzothiadiazole (DTB), although it absorbs a significant part of the solar spectrum, shows a modest absorption in its regions with higher wavelength, corresponding to the yellow and red radiations which, therefore, cannot be converted into others that can be more effectively exploited by the photovoltaic cell (or solar cell).

Efforts have been made in the art in order to find compounds capable of giving comparable or even greater performance, in particular in terms of power generated by the photovoltaic devices wherein they are used, with respect to known benzothiadiazole compounds.

For example, the international patent application WO 2016/046319 in the name of the Applicant, relates to a di-substituted diaryloxybenzoheterodiazole compound having general formula (I):

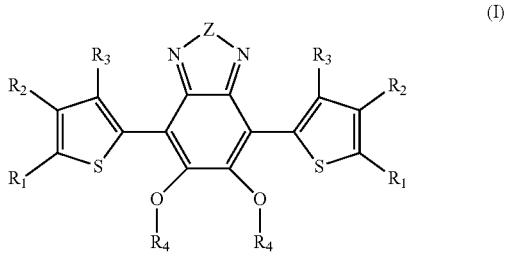

wherein:
- Z represents a sulphur atom, an oxygen atom, a selenium atom; or an $NR_5$ group wherein $R_5$ is selected from $C_1$-$C_{20}$ alkyl groups, preferably $C_1$-$C_8$, linear or branched, or from optionally substituted aryl groups;
- $R_1$, $R_2$ and $R_3$, equal to or different from each other, represent a hydrogen atom; or are selected from $C_1$-$C_{20}$ alkyl groups, preferably $C_1$-$C_8$, linear or branched, optionally containing heteroatoms, optionally substituted cycloalkyl groups, optionally substituted aryl groups, $C_1$-$C_{20}$ alkoxy groups, preferably $C_1$-$C_8$, linear or branched, optionally substituted, optionally substituted phenoxy groups, —$COOR_6$ groups wherein $R_6$ is selected from $C_1$-$C_{20}$ alkyl groups, preferably $C_1$-$C_8$, linear or branched, or is a cyano group;
- or $R_1$ and $R_2$, may optionally be bound together so as to form, together with the carbon atoms to which they are bound, a saturated, unsaturated, or aromatic, cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
- or $R_2$ and $R_3$, may optionally be bound together so as to form, together with the carbon atoms to which they are bound, a saturated, unsaturated, or aromatic, cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
- $R_4$, equal to or different from each other, are selected from optionally substituted aryl groups.

The aforesaid di-substituted diaryloxybenzoheterodiazole compound having general formula (I) is said to be advantageously used as a spectrum converter in luminescent solar concentrators (LSCs) capable, in turn, of improving the performance of photovoltaic devices (or solar devices), selected for example, between photovoltaic cells (or solar cells), photovoltaic modules (or solar modules), either on a rigid support, or on a flexible support.

SUMMARY OF THE DISCLOSURE

The Applicant has now found that some of the di-substituted diaryloxybenzoheterodiazole compounds having general formula (I) described in the aforesaid international patent application WO 2016/046319, in particular diaryloxybenzoheterodiazole compounds di-substituted with thienothiophenic groups having the specific general formula (Ia) below, in addition to being able to give comparable or even greater performances, in particular in terms of power generated by the photovoltaic devices wherein they are used, compared to known benzothiadiazole compounds, they have a high molar extinction coefficient (ε) (i.e. values >20000 $moles^{-1} \times cm^{-1}$). Furthermore, said diaryloxybenzoheterodiazole compounds di-substituted with thienothiophenic groups have high Stokes shift values [i.e. values >4000 $cm^{-1}$ in solution, or values >3000 $cm^{-1}$ in polymethylmethacrylate (PMMA) film]. Furthermore, said diaryloxybenzoheterodiazole compounds di-substituted with thienothiophenic groups have high values of the maximum of the highest energy band in the emission spectrum [i.e. values >600 nm in solution, or values >580 nm in polymethylmethacrylate (PMMA) films]. Moreover, said diaryloxybenzoheterodiazole compounds di-substituted with thienothiophenic groups have, in solution, high values of quantum luminescence efficiency (Φ) (i.e. values >70%). Said diaryloxybenzoheterodiazole compounds di-substituted with thienothiophenic groups are therefore capable of increasing the number of photons effectively convertible into radiation usable by a solar device. Consequently, said diaryloxybenzoheterodiazole compounds di-substituted with thienothiophenic groups can be advantageously used in the construction of luminescent solar concentrators (LSCs). Said luminescent solar concentrators (LSCs) can, in turn, be advantageously used together, for example, with photovoltaic cells (or solar cells), in the construction of photovoltaic devices (or solar devices). In particular, thanks to the fact that the absorption spectrum of said diaryloxybenzoheterodiazole compounds di-substituted with thienothiophenic groups does not overlap with chlorophyll absorption spectrum, said photovoltaic devices (or solar devices) can be advantageously used in the construction of greenhouses.

Therefore, the object of the present disclosure is a diaryloxybenzoheterodiazole compound di-substituted with thienothiophenic groups having general formula (Ia):

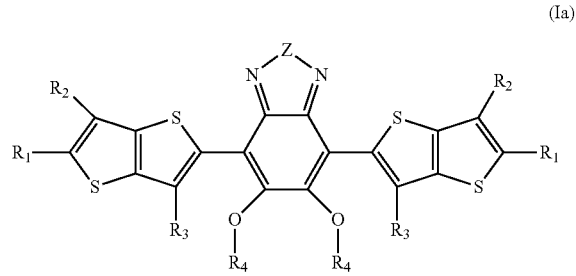

wherein:
- Z represents a sulphur atom, an oxygen atom, a selenium atom; or an $NR_5$ group wherein $R_5$ is selected from $C_1$-$C_{20}$ alkyl groups, preferably linear or branched, or from optionally substituted aryl groups;
- $R_1$, $R_2$ and $R_3$, equal to or different from each other, represent a hydrogen atom; or are selected from $C_1$-$C_{20}$ alkyl groups, preferably $C_1$-$C_5$, linear or branched, optionally containing heteroatoms, optionally substituted cycloalkyl groups, optionally substituted aryl groups, $C_1$-$C_{20}$ alkoxy groups, preferably $C_1$-$C_8$, linear or branched, optionally substituted, —$COOR_5$ groups wherein $R_6$ is selected from $C_1$-$C_{20}$ alkyl groups, preferably $C_1$-$C_8$, linear or branched, or is a cyano group;
- or $R_1$ and $R_2$, may optionally be bound together so as to form, together with the carbon atoms to which they are bound, a saturated, unsaturated, or aromatic, cycle or polycyclic system containing from 3 to 14 carbon atoms, preferably from 4 to 6 carbon atoms, optionally containing one or more heteroatoms such as, for example, oxygen, sulfur, nitrogen, silicon, phosphorus, selenium;
- $R_4$, equal to or different from each other, are selected from optionally substituted aryl groups.

For the purpose of the present description and of the following claims, the definitions of the numerical intervals always comprise the extreme values unless otherwise specified.

For the purpose of the present description and of the following claims, the term "comprising" also includes the terms "which essentially consists of" or "which consists of".

For the purpose of the present description and of the following claims, the term "$C_1$-$C_{20}$ alkyl groups" means linear or branched alkyl groups having from 1 to 20 carbon atoms. Specific examples of $C_1$-$C_{20}$ alkyl groups are: methyl, ethyl, n-propyl, iso-propyl, n-butyl, iso-butyl, t-butyl, pentyl, 2-ethyl-hexyl, hexyl, heptyl, octyl, nonyl, decyl, dodecyl.

For the purpose of the present description and of the following claims, the term "$C_1$-$C_{20}$ alkyl groups optionally containing heteroatoms" means linear or branched, saturated or unsaturated, alkyl groups having from 1 to 20 carbon atoms, wherein at least one of the hydrogen atoms is substituted with a heteroatom selected from: halogens such as, for example, fluorine, chlorine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichlororoethyl, 2,2,3,3-tetrafluoropropyl, 2,2,3,3,3-pentafluoropropyl, perfluoropentyl, perfluoroctyl, perfluorodecyl, oxymethyl, thiometyl, thioethyl, dimethylamino, propylamino, dioctylamino.

For the purpose of the present description and of the following claims, the term "cycloalkyl groups" means cycloalkyl groups having from 3 to 10 carbon atoms. Said cycloalkyl groups can optionally be substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amino groups; nitro groups; aryl groups. Specific examples of cycloalkyl groups are: cyclopropyl, 1,4-dioxin, 2,2-difluorocyclopropyl, cyclobutyl, cyclopentyl, cyclohexyl, methylcyclohexyl, methoxycyclohexyl, fluorocyclohexyl, phenylcyclohexyl.

For the purpose of the present description and of the following claims, the term "aryl groups" means aromatic carbocyclic groups having from 6 to 60 carbon atoms. Said aryl groups can optionally be substituted with one or more groups, equal to or different from each other, selected from: halogen atoms such as, for example, fluorine, chlorine, preferably fluorine; hydroxyl groups; $C_1$-$C_{20}$ alkyl groups; halogenated $C_1$-$C_{20}$ alkyl groups; $C_1$-$C_{20}$ alkoxy groups; cyano groups; amino groups; nitro groups; aryl groups, phenoxy groups. Specific examples of aryl groups are: phenyl, methylphenyl, 2,5-dimethylphenyl, 2,6-dimethylphenyl, 2,4,6-triphenoxylphenyl, trimethylphenyl, trifluoromethylphenyl, di-iso-propylphenyl, t-butylphenyl, methoxyphenyl, hydroxyphenyl, 2-phenoxyphenyl, 2-trifluoromethyl-6-phenoxyphenyl, fluorophenyl, pentafluorophenyl, chlorophenyl, nitrophenyl, dimethylaminophenyl, naphthyl, phenylnaphthyl, phenanthrene, anthracene.

For the purpose of the present description and of the following claims, the term "$C_1$-$C_{20}$ alkoxy groups" means linear or branched alkoxy groups having from 1 to 20 carbon atoms. Said alkoxy groups can optionally be substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxy groups; cyano groups; amino groups; nitro groups. Specific examples of $C_1$-$C_{20}$ alkoxy groups are: methoxy, ethoxy, fluoroethoxy, n-propoxy, iso-propoxy, n-butoxy, n-fluoro-butoxy, iso-butoxy, t-butoxy, pentoxy, hexyloxy, heptyloxy, octyloxy, nonyloxy, decyloxy, dodecyloxy.

For the purpose of the present description and of the following claims, the term "cycle or polycyclic system" means a system containing one or more saturated or unsaturated rings containing 3 to 14 carbon atoms, optionally containing heteroatoms selected from nitrogen, oxygen, sulfur, silicon, selenium, phosphorus. Specific examples of a cycle or polycyclic system are: thieno[3,2-b]thiophene, thiadiazole, benzothiophene, quinoxaline, pyridine.

In accordance with a preferred embodiment of the present disclosure, in said general formula (Ia):
- Z represents a sulfur atom;
- $R_1$, equal to each other, represent a hydrogen atom; or are selected from optionally substituted aryl groups, preferably are 2,6-dimethylphenyl, 2-phenoxyphenyl, 2,4,6-triphenoxyphenyl;
- $R_2$ and $R_3$, equal to each other, represent a hydrogen atom;
- $R_4$ is selected from optionally substituted aryl groups, preferably is phenyl.

Specific examples of diaryloxybenzoheterodiazole compounds di-substituted with thienothiophenic groups having general formula (Ia) useful for the purpose of the present disclosure are reported in Table 1.

TABLE 1

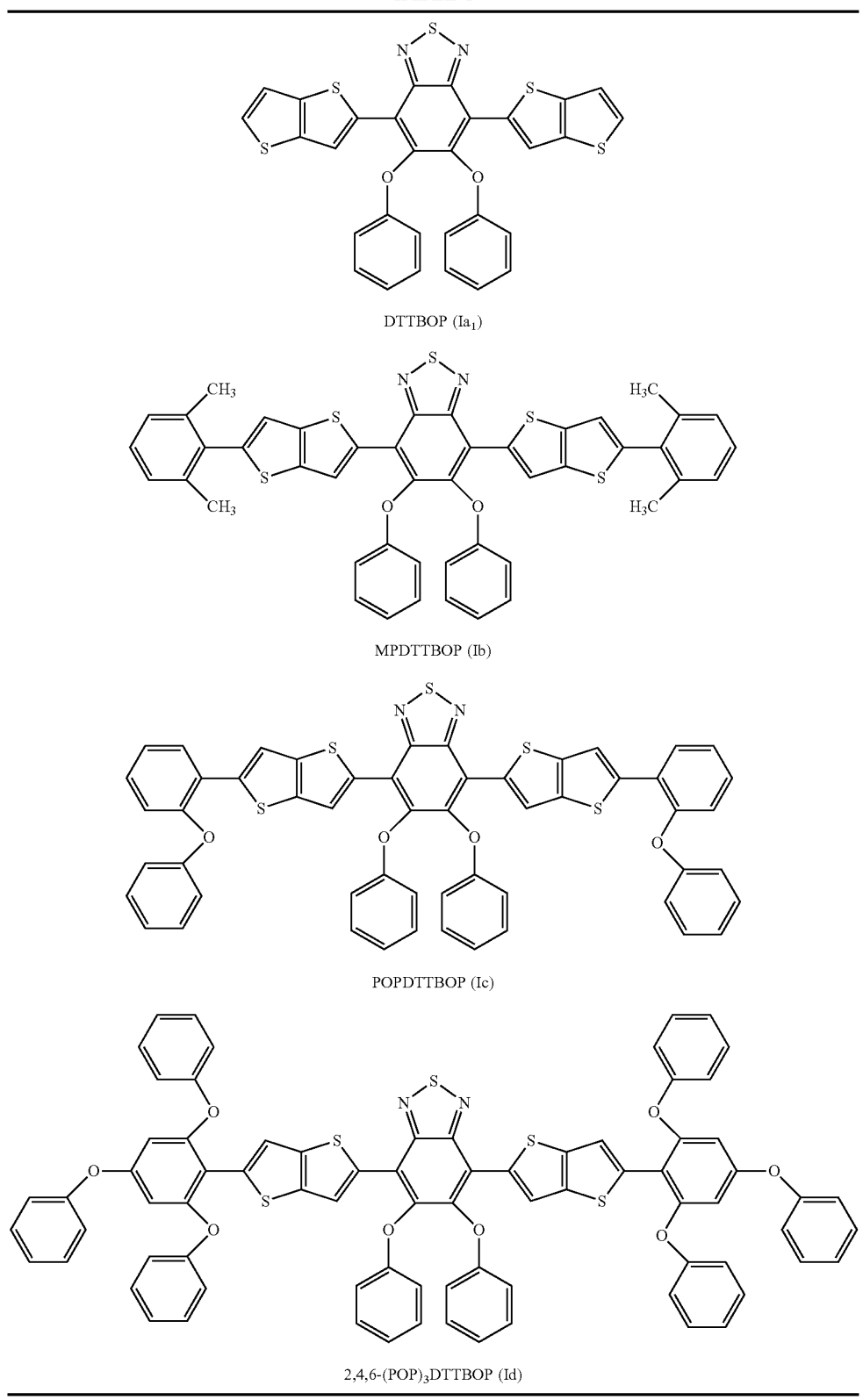

DTTBOP (Ia₁)

MPDTTBOP (Ib)

POPDTTBOP (Ic)

2,4,6-(POP)₃DTTBOP (Id)

The diaryloxybenzoheterodiazole compound di-substituted with thienothiophenic groups having general formula (Ia) object of the present disclosure can be obtained by processes known in the art, operating as described, for example, in the international patent application WO 2016/046319 reported above or in the Italian patent application MI2018000000667, both in the name of the Applicant and incorporated herein by reference. Further details relating to the processes for preparing said diaryloxybenzoheterodiazole compound di-substituted with thienothiophenic groups having general formula (Ia) can be found in the following examples.

Said diaryloxybenzoheterodiazole compound di-substituted with thienothiophenic groups can be advantageously used as a spectrum converter in luminescent solar concentrators (LSCs) capable, in turn, of improving the performance of photovoltaic devices (or solar devices), selected for example, between photovoltaic cells (or solar cells), photovoltaic modules (or solar modules), either on a rigid support, or on a flexible support. More particularly, said photovoltaic devices (or solar devices) can be advantageously used in the construction of greenhouses.

As described above, said diaryloxybenzoheterodiazole compound di-substituted with thienothiophenic groups having general formula (Ia) can be advantageously used as a spectrum converter in luminescent solar concentrators (LSCs) capable, in turn, of improving the performance of photovoltaic devices (or solar devices), such as for example, photovoltaic cells (or solar cells), photovoltaic modules (or solar modules), either on a rigid support, or on a flexible support.

Accordingly, a further object of the present disclosure is a luminescent solar concentrator (LSC) including at least one diaryloxybenzoheterodiazole compound di-substituted with thienothiophenic groups having general formula (Ia).

The diaryloxybenzoheterodiazole compound di-substituted with thienothiophenic groups having general formula (Ia) can be used in said luminescent solar concentrator (LSC) in the following forms: dispersed in the polymer or in the glass, chemically bound to the polymer or glass, in solution, in the form of a gel.

For example, the luminescent solar concentrator (LSC) can contain a transparent matrix, where the term transparent matrix means any transparent material used in the form of a support, a binder, or a material wherein at least one diaryloxybenzoheterodiazole compound di-substituted with thienothiophenic groups having general formula (Ia) is dispersed or incorporated. The material used for the matrix is transparent, as such, to the radiations of interest and, in particular, to the radiations having a frequency comprised in the effective spectrum of the photovoltaic device (or solar device) such as, for example, the photovoltaic cell (or solar cell) wherein it is used. Materials suitable for the purpose of the present disclosure can therefore be selected from transparent materials at least at radiations having a wavelength comprised between 250 nm and 1100 nm.

The transparent matrix which can be used for the purpose of the present disclosure can be selected, for example, from polymeric materials or glassy materials. Said matrix is characterized by a high transparency and a high duration in relation to heat and light. Polymeric materials which can be advantageously used for the purpose of the present disclosure are, for example, polymethylmethacrylate (PMMA), epoxy resins, silicone resins, polyalkylene terephthalates, polycarbonates, polystyrene, polypropylene. Glassy materials that can be advantageously used for the purpose of the present disclosure are, for example, silicas.

In the case wherein the matrix is of the polymeric type, said at least one diaryloxybenzoheterodiazole compound di-substituted with thienothiophenic groups having general formula (Ia) can be dispersed in the polymer of said matrix by, for example, melt dispersion, and subsequent formation of a plate comprising said polymer and said at least one diaryloxybenzoheterodiazole compound di-substituted with thienothiophenic groups having general formula (Ia), operating, for example, according to the technique called "casting". Alternatively, said at least one diaryloxybenzoheterodiazole compound di-substituted with thienothiophenic groups having general formula (Ia) and the polymer of said matrix can be solubilized in at least one solvent obtaining a solution which is deposited on a plate of said polymer, forming a film comprising said at least one diaryloxybenzoheterodiazole compound di-substituted with thienothiophenic groups having general formula (Ia) and said polymer, operating, for example, by using a "Doctor Blade" type film applicator: subsequently, said solvent is allowed to evaporate.

In the case wherein the matrix is of the glassy type, said at least one diaryloxybenzoheterodiazole compound di-substituted with thienothiophenic groups having general formula (Ia) can be solubilized in at least one solvent obtaining a solution which is deposited on a plate of said glassy matrix, forming a film comprising said at least one diaryloxybenzoheterodiazole compound di-substituted with thienothiophenic groups having general formula (Ia), operating, for example, by using a "Doctor Blade" type film applicator: subsequently, said solvent is allowed to evaporate.

A further object of the present disclosure is a photovoltaic device (or solar device) comprising at least one photovoltaic cell (or solar cell), and at least one luminescent solar concentrator (LSC) including at least one diaryloxybenzoheterodiazole compound di-substituted with thienothiophenic groups having general formula (Ia).

Said photovoltaic device (or solar device) can be obtained, for example, by assembling the aforesaid luminescent solar concentrator (LSC) with at least one photovoltaic cell (or solar cell).

A further object of the present disclosure is the use of a photovoltaic device (or solar device) comprising at least one photovoltaic cell (or solar cell), and at least one luminescent solar concentrator (LSC) including at least one diaryloxybenzoheterodiazole compound di-substituted with thienothiophenic groups having general formula (Ia) in the construction of greenhouses.

In accordance with a preferred embodiment of the present disclosure, the aforesaid solar concentrator can be made in the form of a transparent plate obtained by solubilization of said at least one diaryloxybenzoheterodiazole compound di-substituted with thienothiophenic groups having general formula (Ia) and of the polymer of the matrix of the polymeric type in at least one solvent obtaining a solution which is deposited on a plate of said polymer, forming a film comprising said at least one diaryloxybenzoheterodiazole compound di-substituted with thienothiophenic groups having general formula (Ia) and said polymer, operating, for example, by using a "Doctor Blade" type film applicator: subsequently, said solvent is allowed to evaporate. In said photovoltaic devices (or solar devices), said plates can then be coupled to a photovoltaic cell (or solar cell).

DETAILED DESCRIPTION OF THE DISCLOSURE

Figure 1:
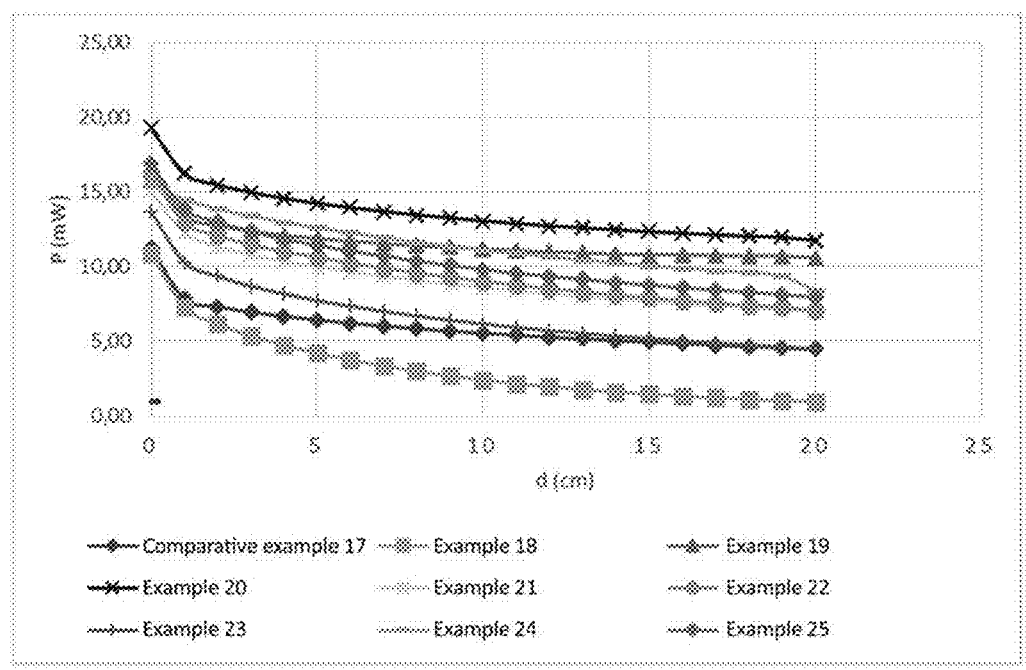
FIG. 1 shows a curve relating to the generated power value (P) as a function of the distance (d) from the edge on which the photovoltaic cell was fixed.

In order to better understand the present disclosure and to put it into practice, some illustrative and non-limiting examples thereof are reported below.

4,7-di-(thien-2'-yl)-2,1,3-benzothiadiazole (DTB) was obtained as described in Example 1 of the international patent application WO 2012/007834 in the name of the Applicant, whose content is incorporated herein by reference.

In the following examples, the analytical techniques and characterization methodologies listed below were used.

Absorption Spectra

The absorption spectra of the solutions in anhydrous dichloromethane ($CH_2Cl_2$) of the obtained diaryloxybenzoheterodiazole compounds di-substituted with thienothiophenic groups having general formula (Ia) or of the polymethylmethacrylate films containing the diaryloxybenzoheterodiazole compounds di-substituted with thienothiophenic groups, in the ultraviolet and in the visible (UV-Vis) (250 nm-800 nm), were acquired in transmission mode using a dual beam and dual monochromator Perkin Elmer λ950 spectrophotometer, with a 2.0 nm bandwidth and 1.0 nm step. From these spectra the ideal wavelength was identified (generally λ=470 nm-510 nm) for the subsequent photoluminescence measurements, corresponding to the zone of maximum absorption of the examined diaryloxybenzoheterodiazole compound di-substituted with thienothiophenic groups having general formula (Ia).

Molar Extinction Coefficient (ε)

The molar extinction coefficient (ε) in solution of anhydrous dichloromethane ($CH_2Cl_2$) of the obtained diaryloxybenzoheterodiazole compounds di-substituted with thienothiophenic groups having general formula (Ia) was obtained as follows.

For this purpose, at least 3 solutions of known titre were prepared for each diaryloxybenzoheterodiazole compound di-substituted with thienothiophenic groups having general formula (Ia): the UV-visible absorption spectrum was then recorded for each solution and, maintaining the optical path of 1 cm, the absorbance value relative to the spectral position of the maximum of the absorption band under examination was read.

The molar extinction coefficient (ε) was then calculated using the Lambert-Beer law (A=εbc, wherein ε is the molar extinction coefficient, b is the optical path, c is the molar concentration, A is the absorbance) according to what is reported by N. J. Turro, V. Ramamurthy and J. C. Scaiano in "*Modern Molecular Photochemistry of Organic Molecules*" (2010), ISBN 978-1-891389-25-2, pages 215-217.

Emission Spectra

The emission spectra of the solutions in anhydrous dichloromethane ($CH_2Cl_2$) of the obtained diaryloxybenzoheterodiazole compounds di-substituted with thienothiophenic groups having general formula (Ia) or of the polymethylmethacrylate films containing the obtained diaryloxybenzoheterodiazole compounds di-substituted with thienothiophenic groups having general formula (Ia) were recorded using a Horiba Jobin Yvon Fluorolog 3 spectrofluorimeter, operating in "right-angle" configuration and exciting at the selected wavelength as described above (i.e. ideal wavelength).

Stokes Shift

The Stokes shift was obtained from the analysis of the absorption and emission spectra for each obtained diaryloxybenzoheterodiazole compound di-substituted with thienothiophenic groups having general formula (Ia), and was calculated as the difference, in frequency units ($cm^{-1}$), between the spectral positions of the maxima of the absorption band and of the emission band.

Luminescence Quantum Efficiency (Φ)

The luminescence quantum efficiency (Φ) of the solutions in anhydrous dichloromethane ($CH_2Cl_2$) of the obtained diaryloxybenzoheterodiazole compounds di-substituted with thienothiophenic groups having general formula (Ia) was obtained using the comparative method reported by A. T. R. Williams, S. A. Winfield and J. N. Miller in "Analyst" (1983), Vol. 108, page 1067.

For this purpose, 4,7-di-(thien-2'-yl)-2,1,3-benzothiadiazole (DTB) dissolved in anhydrous dichloromethane ($CH_2Cl_2$) (0.9% by weight) was used as a reference standard, luminescence quantum efficiency (Φ) equal to 90%.

EXAMPLE 1

Synthesis of 4,7-dithienothienyl-5,6-diphenoxy-2,1,3-benzothiadiazole Having Formula ($Ia_1$) (DTT-BOP)

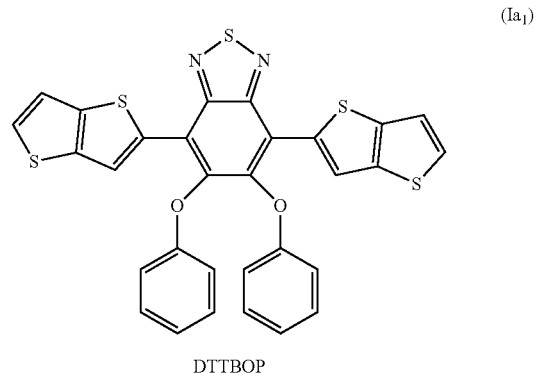

DTTBOP (1) Synthesis of 4,7-dibromo-5,6-diphenoxy-2,1,3-benzothiadiazole Having Formula (a)

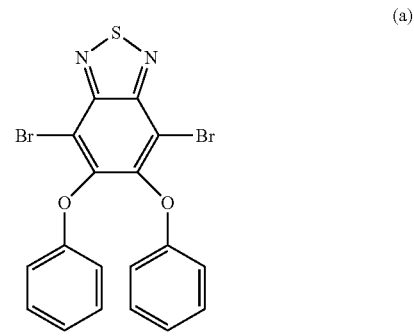 [SMILES: Brc1c(Oc2ccccc2)c(Oc2ccccc2)c(Br)c2nsnc12]

In a 100 ml flask, equipped with magnetic stirring, thermometer and coolant, in an inert atmosphere, phenol (Aldrich) (2.9 g; 2.8 ml, 31.6 mmoles) and potassium carbonate (Aldrich) (4.4 g; 31.6 mmoles) were added to a 0.3 M solution of 4,7-dibromo-5,6-difluoro-2,1,3-benzothiadiazole (Sunatech) (4.35 g; 13.2 mmoles) in anhydrous N,N-dimethylformamide (Aldrich) (44 ml): the obtained reaction mixture was heated to 82° C. and kept, under stirring, at said temperature, for 12 hours. Subsequently, after adding 200 ml of distilled water, the precipitate obtained was recovered by filtration, washed to neutral with distilled water (30 ml) and subsequently dried under vacuum, obtaining 6.3 g (13.2 mmoles) of 4,7-dibromo-5,6-diphenoxy-2,1,3-benzothiadiazole having formula (a) (yield=100%).

(2) Synthesis of 2-tri-n-butylstannylthienothiophene Having Formula (b)

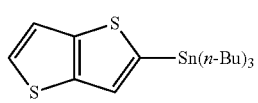

In a 100 ml flask, equipped with magnetic stirring and thermometer, in an inert atmosphere, n-butyllithium (Aldrich) (1.6 M solution in hexane) (2.5 ml; 4 mmoles) was added to a 0.12 M solution of 2,6-thienothiophene (Aldrich) (0.5 g; 3.6 mmol) in anhydrous tetrahydrofuran (Aldrich) (30 ml) at −78° C., by dripping: the reaction mixture obtained was kept under stirring and the temperature was brought to −50° C. in 3 hours. Subsequently, after placing the flask in a bath containing acetone and dry ice at −78° C., tri-n-butylstannyl chloride (Aldrich) (1.4 g; 1.2 ml; 4.3 mmoles) was added by dripping. After 15 minutes the flask was removed from the bath, the temperature was allowed to rise to 20° C. and the reaction mixture was kept, under stirring, at said temperature, for 12 hours. Subsequently, the reaction mixture, after addition of a saturated aqueous solution of sodium bicarbonate (Aldrich) (20 ml), was extracted with ethyl ether (Aldrich) (3×25 ml). The organic phase obtained was washed with a saturated aqueous solution of sodium bicarbonate (Aldrich) (20 ml), and subsequently anhydrified on sodium sulphate (Aldrich). The residual solvent was removed by distillation under reduced pressure obtaining 2-tri-n-butylstannylthienothiophene having formula (b) which was used as follows.

(3) Synthesis of 4,7-dithienothienyl-5,6-diphenoxy-2,1,3-benzothiadiazole Having Formula (Ia₁) (DTTBOP)

In a 100 ml flask, equipped with magnetic stirring, thermometer and coolant, in an inert atmosphere, 2-tri-n-butylstannylthienothiophene having formula (b) obtained as described above, was dissolved in anhydrous toluene (Aldrich) (30 ml) obtaining a solution to which 4,7-dibromo-5,6-diphenoxy-2,1,3-benzothiadiazole having formula (a), obtained as described above (0.71 g; 1.5 mmoles), was added. After having removed the air present by 3 vacuum/nitrogen cycles, tris-dibenzylideneacetone dipalladium (Aldrich) (40 mg; 0.04 mmoles) and tris-o-tolylphosphine (Aldrich) (50 mg; 0.16 mmoles) were added obtaining a reaction mixture which was immersed into a pre-heated bath at 110° C. and kept, under stirring, at said temperature, for 12 hours. Subsequently, the reaction mixture was poured into distilled water (50 ml) and extracted with dichloromethane (CH₂Cl₂) (Aldrich) (3×25 ml): the obtained organic phase was washed to neutral with distilled water (3×25 ml) and subsequently anhydrified on sodium sulphate (Aldrich).

After having removed most of the residual solvent by distillation under reduced pressure, the residue obtained was added, by dripping, to 50 ml of methanol, obtaining a precipitate which was recovered by filtration and subsequently purified by elution on a silica gel chromatographic column [eluent in n-heptane (Aldrich)/dichloromethane (Aldrich) gradient from 9/1 to 8/2 to 6/4 (v/v)] obtaining 0.9 g (1.2 mmol) of 4,7-dithienothienyl-5,6-diphenoxy-2,1,3-benzothiadiazole having formula (Ia₁) (DTTBOP) (yield=80%).

EXAMPLE 2

Synthesis of 4,7-di-2-(2,6-dimethylphenyl)thienothienyl-5,6-diphenoxy-2,1,3-benzothiadiazole Having Formula (Ib) (MPDTTBOP)

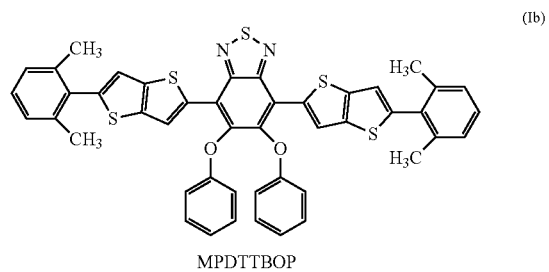 [SMILES: Cc1cccc(C)c1-c1cc2sc(-c3c(Oc4ccccc4)c(Oc4ccccc4)c(-c4cc5sc(-c6c(C)cccc6C)cc5s4)c4nsnc34)cc2s1]

MPDTTBOP (1) Synthesis of 2-bromothienothiophene Having Formula (c)

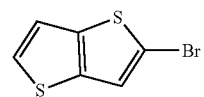

In a 100 ml flask, equipped with magnetic stirring and thermometer, in an inert atmosphere, N-bromosuccinimide (1.95 g; 11.02 mmoles) was added to a 0.25 M solution of 2,6-thienothiophene (Aldrich) (1.4 g; 10.1 mmoles) in dichloromethane (CH₂Cl₂) (Aldrich) (40 ml): the reaction mixture obtained was kept, under stirring, at room temperature (25° C.), in the dark, for 12 hours. Subsequently, the reaction mixture was poured into distilled water (50 ml) and extracted with dichloromethane (CH₂Cl₂) (Aldrich) (3×25 ml): the obtained organic phase was washed to neutral with distilled water (3×25 ml) and subsequently anhydrified on sodium sulphate (Aldrich). After having removed the residual solvent by distillation under reduced pressure, the obtained residue was purified by elution on a silica gel chromatographic column [eluent: n-heptane (Aldrich)] obtaining 2.15 g (9.8 mmoles) of 2-bromothienothiophene having formula (c) (yield=97%).

(2) Synthesis of 2-(2,6-dimethylphenyl)thienothiophene Having Formula (d)

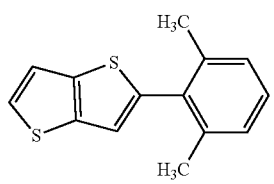

In a 100 ml flask, equipped with magnetic stirring and thermometer, in an inert atmosphere, 2,6-dimethylphenyl-boronic acid (Aldrich) (0.85 g; 5.66 mmoles) and 8.7 ml of a 2 M aqueous solution of potassium carbonate (Aldrich) (2.4 g; 17.4 mmoles) were added to a 0.17 M solution of 2-bromothienothiophene having formula (c) obtained as described above (0.96 g; 4.35 mmoles) in 1,4-dioxane (Aldrich) (26 ml). After having removed the air present by 3 vacuum/nitrogen cycles, tetrakisphenylphosphine-palladium (Aldrich) (0.11 g; 0.095 mmoles) was added obtaining a reaction mixture which was immersed in a bath pre-heated to 85° C. and kept, under stirring, at said temperature, for 18 hours. Subsequently, the reaction mixture was poured into distilled water (50 ml) and extracted with dichloromethane ($CH_2Cl_2$) (Aldrich) (3×25 ml): the obtained organic phase was washed to neutral with distilled water (3×25 ml) and subsequently anhydrified on sodium sulphate (Aldrich). After having removed the residual solvent by distillation under reduced pressure, the obtained residue was purified by elution on a silica gel chromatographic column [eluent: n-heptane (Aldrich)] obtaining 0.64 g (2.6 mmoles) of 2-(2,6-dimethylphenyl)thienothiophene having formula (d) (yield=60%).

(3) Synthesis of 2-tri-n-butylstannyl-5-(2,6-dimethylphenyl)thienothiophene Having Formula (e)

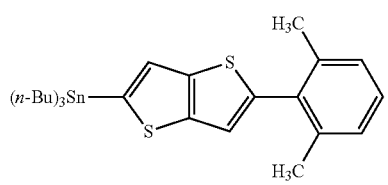

In a 100 ml flask, equipped with magnetic stirring and thermometer, in an inert atmosphere, n-butyllithium (Aldrich) (1.6 M solution in hexane) (1.8 ml; 2.86 mmoles) was added to a 0.12 M solution of 2-(2,6-dimethylphenyl)thienothiophene having formula (d) (0.64 g; 2.6 mmol) obtained as described above in anhydrous tetrahydrofuran (Aldrich) (22 ml), at −78° C., by dripping: the reaction mixture obtained was kept under stirring and the temperature was brought to −50° C. in 3 hours. Subsequently, after placing the flask in a bath containing acetone and dry ice at −78° C., tri-n-butylstannyl chloride (Aldrich) (1 g; 0.85 ml; 3.12 mmoles) was added by dripping. After 15 minutes the flask was removed from the bath, the temperature was allowed to rise to 20° C. and the reaction mixture was kept, under stirring, at said temperature, for 12 hours. Subsequently, the reaction mixture, after addition of a saturated aqueous solution of sodium bicarbonate (Aldrich) (20 ml), was extracted with ethyl ether (Aldrich) (3×25 ml). The organic phase obtained was washed with a saturated aqueous solution of sodium bicarbonate (Aldrich) (20 ml), and subsequently anhydrified on sodium sulphate (Aldrich). The residual solvent was removed by distillation under reduced pressure obtaining 2-tri-n-butylstannyl-5-(2,6-dimethylphenyl)thienothiophene having formula (e) which was used as follows.

(4) Synthesis of 4,7-di-(2,6-dimethylphenyl) thienothienyl-5,6-diphenoxy-2,1,3-benzothiadiazole Having Formula (Ib) (MPDTTBOP)

In a 100 ml flask, equipped with magnetic stirring, thermometer and coolant, under an argon flow, 2-tri-n-butylstannyl-5-(2,6-dimethylphenyl)thienothiophene having formula (e) obtained as described above was dissolved in anhydrous toluene (Aldrich) (20 ml) obtaining a solution to which 4,7-dibromo-5,6-diphenoxy-2,1,3-benzothiadiazole having formula (a), obtained as described in Example 1 (0.48 g; 1 mmole), was added. After having removed the air present by 3 vacuum/nitrogen cycles, tris-dibenzylideneacetone dipalladium (Aldrich) (22.2 mg; 0.02 mmoles) and tris-o-tolylphosphine (Aldrich) (28 mg; 0.09 mmoles) were added obtaining a reaction mixture which was immersed into a pre-heated bath at 110° C. and kept, under stirring, at said temperature, for 12 hours. Subsequently, the reaction mixture was poured into distilled water (50 ml) and extracted with dichloromethane ($CH_2Cl_2$) (Aldrich) (3×25 ml): the obtained organic phase was washed to neutral with distilled water (3×25 ml) and subsequently anhydrified on sodium sulphate (Aldrich). After having removed most of the residual solvent by distillation under reduced pressure, the residue obtained was added, by dripping, to 50 ml of methanol, obtaining a precipitate which was recovered by filtration and subsequently purified by elution on a silica gel chromatographic column [eluent in n-heptane (Aldrich)/dichloromethane (Aldrich) gradient from 100/0 to 95/5 to 8/2 (v/v)] obtaining 0.6 g (0.75 mmoles) of 4,7-di-(2,6-dimethylphenyl)thienothienyl-5,6-diphenoxy-2,1,3-benzothiadiazole having formula (Ib) (MPDTTBOP) (yield=75%).

EXAMPLE 3

Synthesis of 4,7-di-2-(2-phenoxyphenyl)thienothienyl-5,6-diphenoxy-2,1,3-benzothiadiazole Having Formula (Ic) (POPDTTBOP)

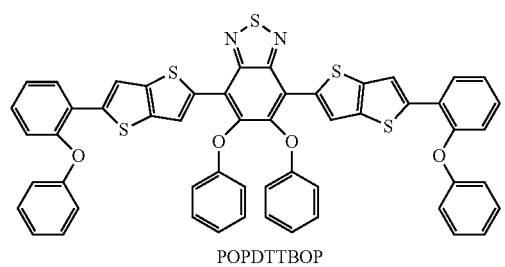

POPDTTBOP

(1) Synthesis of 2-(2-phenoxyphenyl)thienothiophene Having Formula (f)

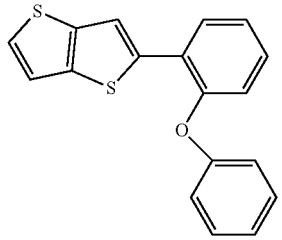

(f)

In a 100 ml flask, equipped with magnetic stirring and thermometer, in an inert atmosphere, 2-phenoxyphenylboronic acid (Aldrich) (1.14 g; 5.33 mmol) and 8.2 ml of an 2 M aqueous solution of potassium carbonate (Aldrich) (2.3 g; 16.4 mmoles) were added to a 0.17 M solution of 2-bromothienothiophene having formula (c) obtained as described in Example 2 (0.9 g; 4.1 mmol) in 1,4-dioxane (Aldrich) (24 ml). After having removed the air present by 3 vacuum/nitrogen cycles, tetrakisphenylphosphine-palladium (Aldrich) (0.97 g; 0.084 mmoles) was added obtaining a reaction mixture which was immersed in a bath pre-heated to 85° C. and kept, under stirring, at said temperature, for 18 hours. Subsequently, the reaction mixture was poured into distilled water (50 ml) and extracted with dichloromethane ($CH_2Cl_2$) (Aldrich) (3×25 ml): the obtained organic phase was washed to neutral with distilled water (3×25 ml) and subsequently anhydrified on sodium sulphate (Aldrich). After having removed the residual solvent by distillation under reduced pressure, the obtained residue was purified by elution on a silica gel chromatographic column [eluent: n-heptane (Aldrich)] obtaining 0.8 g (2.6 mmoles) of 2-(2-phenoxyphenyl)thienothiophene having formula (f) (yield=63%).

(2) Synthesis of 2-tri-n-butylstannyl-5-(2-phenoxyphenyl)thienothiophene Having Formula (g)

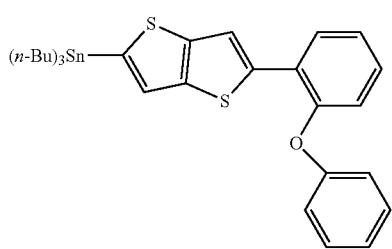

(g)

In a 100 ml flask, equipped with magnetic stirring and thermometer, in an inert atmosphere, n-butyllithium (Aldrich) (1.6 M solution in hexane) (1.8 ml; 2.86 mmoles) was added to a 0.12 M solution of 2-(2-phenoxyphenyl)thienothiophene having formula (f) (0.8 g; 2.6 mmoles) obtained as described above in anhydrous tetrahydrofuran (Aldrich) (22 ml), at −78° C., by dripping: the reaction mixture obtained was kept under stirring and the temperature was brought to −50° C. in 3 hours. Subsequently, after placing the flask in a bath containing acetone and dry ice at −78° C., tri-n-butylstannyl chloride (Aldrich) (1 g; 0.85 ml; 3.12 mmoles) was added by dripping. After 15 minutes the flask was removed from the bath, the temperature was allowed to rise to 20° C. and the reaction mixture was kept, under stirring, at said temperature, for 12 hours. Subsequently, the reaction mixture, after addition of a saturated aqueous solution of sodium bicarbonate (Aldrich) (20 ml), was extracted with ethyl ether (Aldrich) (3×25 ml). The organic phase obtained was washed with a saturated aqueous solution of sodium bicarbonate (Aldrich) (20 ml), and subsequently anhydrified on sodium sulphate (Aldrich). The residual solvent was removed by distillation under reduced pressure obtaining 2-tri-n-butylstannyl-5-(2-phenoxyphenyl)thienothiophene having formula (g) which was used as follows.

(3) Synthesis of 4,7-di-2-(2-phenoxyphenyl)thienothienyl-5,6-diphenoxy-2,1,3-benzothiadiazole Having Formula (Ic) (POPDTTBOP)

In a 100 ml flask, equipped with magnetic stirring, thermometer and coolant, under an argon flow, 2-tri-n-butylstannyl-5-(2-phenoxyphenyl)thienothiophene having formula (g) obtained as described above was dissolved in anhydrous toluene (Aldrich) (20 ml) obtaining a solution to which 4,7-dibromo-5,6-diphenoxy-2,1,3-benzothiadiazole having formula (a), obtained as described in Example 1 (0.48 g; 1 mmole), was added. After having removed the air present by 3 vacuum/nitrogen cycles, tris-dibenzylideneacetone dipalladium (Aldrich) (22.2 mg; 0.02 mmoles) and tris-o-tolylphosphine (Aldrich) (28 mg; 0.09 mmoles) were added obtaining a reaction mixture which was immersed into a pre-heated bath at 110° C. and kept, under stirring, at said temperature, for 12 hours. Subsequently, the reaction mixture was poured into distilled water (50 ml) and extracted with dichloromethane ($CH_2Cl_2$) (Aldrich) (3×25 ml): the obtained organic phase was washed to neutral with distilled water (3×25 ml) and subsequently anhydrified on sodium sulphate (Aldrich). After having removed most of the residual solvent by distillation under reduced pressure, the residue obtained was added, by dripping, to 50 ml of methanol, obtaining a precipitate which was recovered by filtration and subsequently purified by elution on a silica gel chromatographic column [eluent in n-heptane (Aldrich)/dichloromethane (Aldrich) gradient from 100/0 to 95/5 to 8/2 (v/v)] obtaining 0.65 g (0.7 mmoles) of 4,7-di-2-(2-phenoxyphenyl)thienothienyl-5,6-diphenoxy-2,1,3-benzothiadiazole having formula (Ic) (POPDTTBOP) (yield=70%).

EXAMPLE 4

Synthesis of 4,7-di-2-(2,4,6-triphenoxyphenyl)thienothienyl-5,6-diphenoxy-2,1,3-benzothiadiazole Having Formula (Id) (2,4,6-(POP)₃DTTBOP)

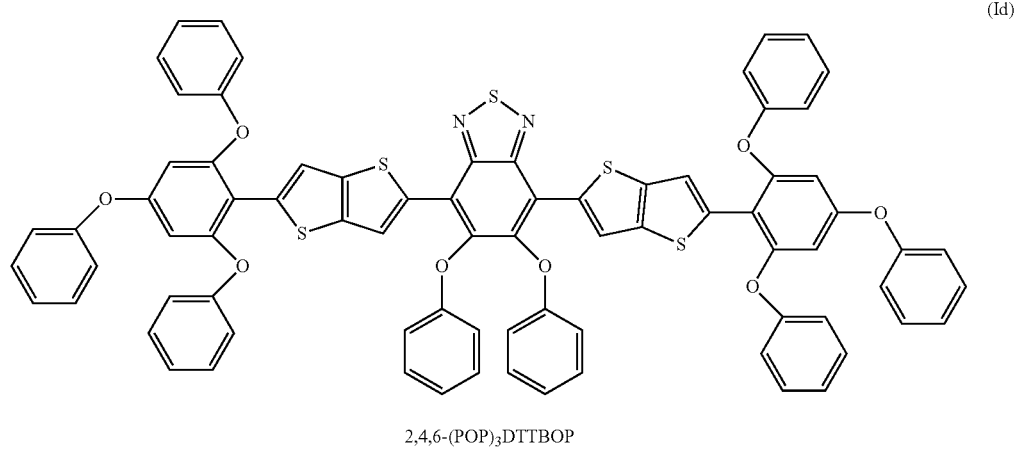 [SMILES: c1ccc(Oc2cc(Oc3ccccc3)c(-c3cc4sc(-c5c(Oc6ccccc6)c(Oc6ccccc6)c(-c6cc7sc(-c8c(Oc9ccccc9)cc(Oc9ccccc9)cc8Oc8ccccc8)cc7s6)c6nsnc56)cc4s3)c(Oc3ccccc3)c2)cc1]

2,4,6-(POP)₃DTTBOP (1) Synthesis of 2,4,6-triphenoxy-1-bromothienothiophene Having Formula (h)

(2) Synthesis of 2-(2,4,6-triphenoxyphenyl)thienothiophene Having Formula (i)

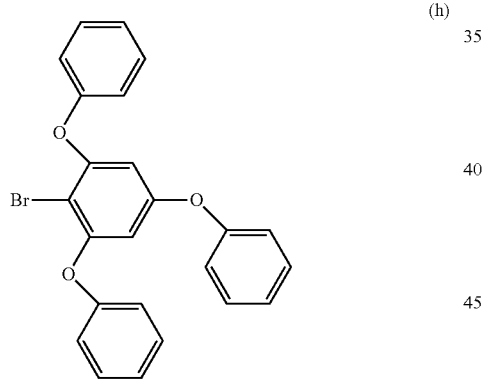

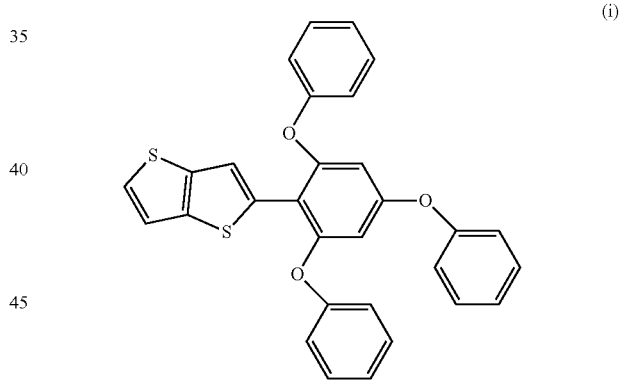

In a microwave vial were loaded: 2,4-trifluoro-1-bromobenzene (Aldrich) (1.6 g; 7.6 mmoles), phenol (3.4 g; 36.2 mmoles), potassium carbonate (Aldrich) (5 g; 36.2 mmoles) and N-methylpyrrolidone (Aldrich) (26 ml). After shaking the reaction mixture obtained, under an argon flow, the vial was closed with the appropriate plug and inserted in an 80 ml reactor: the reaction ramp was set from 25° C. to 220° C. in 4 minutes. The reaction mixture was kept in the reactor, at 220° C., for 3 hours, subsequently recovered, poured into distilled water (100 ml) and extracted with ethyl ether (Aldrich) (3×25 ml): the organic phase obtained was washed to neutral with distilled water (3×25 ml) and subsequently anhydrified on sodium sulphate (Aldrich). After having removed the residual solvent by distillation under reduced pressure, the obtained residue was purified by elution on a silica gel chromatographic column [eluent: n-heptane (Aldrich)] obtaining 2.3 g of 2,4,6-triphenoxy-1-bromobenzene having formula (h) (yield=70%).

In a 100 ml flask, equipped with magnetic stirring and thermometer, in an inert atmosphere, 2-tri-n-butylstannylthienothiophene having formula (b) obtained as described in Example 1 was added to a 0.16 M solution of 2,4,6-triphenoxy-1-bromobenzene having formula (h) (2.1 g; 5 mmoles) obtained as described above, in anhydrous toluene (Aldrich) (32 ml). After having removed the air present by 3 vacuum/nitrogen cycles, tris-dibenzylideneacetone dipalladium (Aldrich) (52.3 mg; 0.06 mmoles) and tris-o-tolylphosphine (Aldrich) (65.4 mg; 0.21 mmoles) were added obtaining a reaction mixture which was immersed into a pre-heated bath at 110° C. and kept, under stirring, at said temperature, for 12 hours. Subsequently, the reaction mixture was poured into distilled water (50 ml) and extracted with dichloromethane (CH₂Cl₂) (Aldrich) (3×25 ml): the obtained organic phase was washed to neutral with distilled water (3×25 ml) and subsequently anhydrified on sodium sulphate (Aldrich). After having removed most of the residual solvent by distillation under reduced pressure, the residue obtained was added, by dripping, to 50 ml of methanol, obtaining a precipitate which was recovered by filtration and subsequently purified by elution on a silica gel chromatographic column [eluent in n-heptane (Aldrich)/ dichloromethane (Aldrich) gradient from 100/0 to 95/5 to 85/15 (v/v)] obtaining 1 g (2 mmoles) of 2-(2,4,6-triphenoxyphenyl)thienothiophene having formula (i) (yield=41%).

(3) Synthesis of 2-tri-n-butylstannyl-5-(2,4,6-triphenoxyphenyl) thienothiophene Having Formula (1)

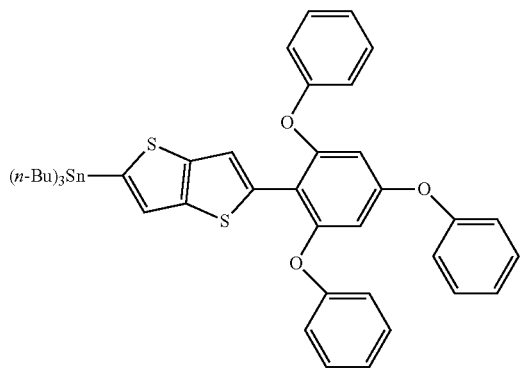

(l)

In a 100 ml flask, equipped with magnetic stirring and thermometer, in an inert atmosphere, n-butyllithium (Aldrich) (1.6 M solution in hexane) (0.8 ml; 1.3 mmoles) was added to a 0.08 M solution of 2-(2,4,6-triphenoxyphenyl) thienothiophene having formula (i) (0.58 g; 1.17 mmoles) obtained as described above, in anhydrous tetrahydrofuran (Aldrich) (15 ml), at −78° C., by dripping: the reaction mixture obtained was kept under stirring and the temperature was brought to −50° C. in 3 hours. Subsequently, after placing the flask in a bath containing acetone and dry ice at −78° C., tri-n-butylstannyl chloride (Aldrich) (0.46 g; 0.38 ml; 1.4 mmoles) was added by dripping. After 15 minutes the flask was removed from the bath, the temperature was allowed to rise to 20° C. and the reaction mixture was kept, under stirring, at said temperature, for 12 hours. Subsequently, the reaction mixture, after addition of a saturated aqueous solution of sodium bicarbonate (Aldrich) (20 ml), was extracted with ethyl ether (Aldrich) (3×25 ml). The organic phase obtained was washed with a saturated aqueous solution of sodium bicarbonate (Aldrich) (20 ml), and subsequently anhydrified on sodium sulphate (Aldrich). The residual solvent was removed by distillation under reduced pressure to obtain 2-tri-n-butylstannyl-5-(2,4,6-triphenoxyphenyl)thieno-thiophene having formula (1) which was used as follows.

(4) Synthesis of 4,7-di-2-(2,4,6-triphenoxyphenyl) thienothienyl-5,6-diphenoxy-2,1,3-benzothiadiazole Having Formula (Id) (2,4,6-(POP)₃DTTBOP)

In a 100 ml flask, equipped with magnetic stirring, thermometer and coolant, under an argon flow, 2-tri-n-butylstannyl-5-(2,4,6-triphenoxyphenyl)thienothiophene having formula (1) obtained as described above was dissolved in anhydrous toluene (Aldrich) (10 ml) obtaining a solution to which 4,7-dibromo-5,6-diphenoxy-2,1,3-benzothiadiazole having formula (IVa) obtained as described in Example 1 (0.22 g; 0.46 mmoles), was added. After having removed the air present by 3 vacuum/nitrogen cycles, tris-dibenzylideneacetone dipalladium (Aldrich) (11 mg; 0.012 mmoles) and tris-o-tolylphosphine (Aldrich) (14 mg; 0.046 mmoles) were added obtaining a reaction mixture which was immersed into a pre-heated bath at 110° C. and kept, under stirring, at said temperature, for 12 hours. Subsequently, the reaction mixture was poured into distilled water (50 ml) and extracted with dichloromethane ($CH_2Cl_2$) (Aldrich) (3×25 ml): the obtained organic phase was washed to neutral with distilled water (3×25 ml) and subsequently anhydrified on sodium sulphate (Aldrich). After having removed most of the residual solvent by distillation under reduced pressure, the residue obtained was added, by dripping, to 50 ml of methanol, obtaining a precipitate which was recovered by filtration and subsequently purified by elution on a silica gel chromatographic column [eluent in n-heptane (Aldrich)/ dichloromethane (Aldrich) gradient from 100/0 to 95/5 to 9/1 to 8/2 to 7/3 to 1/1 (v/v)] obtaining 0.4 g (0.3 mmoles) of 4,7-di-2-(2,4,6-triphenoxyphenyl)thienothienyl-5,6-diphenoxy-2,1,3-benzothiadiazole having formula (Id) (2,4,6-(POP)₃DTTBOP) (yield=67%).

EXAMPLE 5

Preparation of a polymethylmethacrylate (PMMA) Film Containing 4,7-dithienothienyl-5,6-diphenoxy-2,1,3-benzothiadiazole Having Formula (Ia₁) (DTTBOP) for the Measurement of the Spectroscopic Properties The measurement of the spectroscopic properties of 4,7-dithienothienyl-5,6-diphenoxy-2,1,3-benzothiadiazole having formula (Ia₁), obtained according to what is described in Example 1, was carried out by dispersing said compound in an Altuglas VSUVT 100 (PMMA) polymethylmethacrylate matrix.

In this regard, 2 g of Altuglas VSUVT 100 (PMMA) polymethylmethacrylate and 4 ml of an anhydrous dichloromethane ($CH_2Cl_2$) solution (Aldrich) containing 4,7-dithienothienyl-5,6-diphenoxy-2,1,3-benzothiadiazole having formula (Ia₁) (concentration DTTBOP=$3.37 \times 10^{-5}$ moles/liter) were introduced into a 12 ml vial. The mixture obtained was kept in motion, at 25° C., by means of a shaking machine, for 16 hours, until complete dissolution of the Altuglas VSUVT 100 (PMMA) polymethylmethacrylate.

Subsequently, part of the solution thus obtained was deposited on a quartz plate (2 cm×2 cm) with optical surfaces, kept in a perfectly horizontal position. Subsequently, the plate was covered with a suitably sized beaker, so that an environment almost saturated with dichloromethane ($CH_2Cl_2$) is formed, thus obtaining a slow evaporation of dichloromethane ($CH_2Cl_2$) in order to prevent the formation of micro bubbles inside the film.

Once the solvent was completely evaporated (3 days), the Altuglas VSUVT 100 (PMMA) polymethylmethacrylate film containing 4,7-dithienothienyl-5,6-diphenoxy-2,1,3-benzothiadiazole having formula (Ia₁) was detached from the quartz support.

On the film thus obtained, the absorption spectrum, the emission spectrum and the Stokes shift were acquired, operating as described above: the values obtained are reported in Table 2.

EXAMPLE 6-8

Preparation of polymethylmethacrylate (PMMA) Films Containing Compounds Having General Formula (Ia) for the Measurement of Spectroscopic Properties Following the procedure described in Example 5, Altuglas VSUVT 100 (PMMA) polymethylmethacrylate films containing the compounds having formula (Ib) (MPDTTBOP) (solution concentration of MPDTTBOP=6.21×10$^{-5}$ moles/liter), formula (Ic) (POPDTTBOP) (solution concentration of POPDTTBOP=3.83×10$^{-5}$ moles/liter), and formula (Id) (2,4,6-(POP)$_3$DTTBOP) (solution concentration of 2,4,6-(POP)$_3$DTTBOP=2.24×10$^{-5}$ moles/liter), prepared as reported in Examples 2, 3 and 4, respectively, were prepared.

On each film thus obtained, the absorption spectrum, the emission spectrum and the Stokes shift were acquired, operating as described above: the values obtained are reported in Table 2.

Table 2 reports, in the order: the number of the example (Example), the number that refers to the formula of the compound used (Compound formula), the number of the example wherein the compound has been prepared (Prep. example), the value of the maximum of the lowest energy band in the absorption spectrum [$\lambda_{max}$ (abs.)] expressed in (nm), the value of the maximum of the highest energy band in the emission spectrum [$\lambda_{max}$ (emiss.)] expressed in (nm) and finally the value of the Stokes shift expressed in (cm$^{-1}$)

TABLE 2

| Example | Compound formula | Prep. example | $\lambda_{max}$ (abs.) (nm) | $\lambda_{max}$ (emiss.) (nm) | Stokes shift (cm$^{-1}$) |
|---|---|---|---|---|---|
| 5 | (Ia$_1$) | 1 | 474 | 584 | 3272 |
| 6 | (Ib) | 2 | 486 | 596 | 3798 |
| 7 | (Ic) | 3 | 512 | 622 | 3454 |
| 8 | (Id) | 4 | 513 | 624 | 3468 |

EXAMPLE 9

Preparation of a Solution Containing 4,7-dithienothienyl-5,6-diphenoxy-2,1,3-benzothiadiazole Having Formula (Ia) (DTTBOP) for the Measurement of the Spectroscopic Properties 1.78 mg (2.9×10$^{-3}$ mmoles) of 4,7-dithienothienyl-5,6-diphenoxy-2,1,3-benzothiadiazole having formula (Ia$_1$) (DTTBOP), obtained according to what described in Example 1, and 50 ml of anhydrous dichloromethane (CH$_2$Cl$_2$) were introduced into a 50 ml flask: the mixture obtained was left, under stirring, at room temperature (25° C.), for 16 hours, until a homogeneous solution was obtained. Subsequently, an aliquot of the solution obtained was transferred to a 1 cm quartz cell, and the absorption spectrum, the molar extinction coefficient (ε), the emission spectrum and the Stokes shift were acquired, operating as described above: the values obtained are reported in Table 3.

ESEMPI 10-12

Preparation of Solutions Containing Compounds Having General Formula (Ia) for the Measurement of the Spectroscopic Properties Following the procedure described in Example 9, solutions in anhydrous dichloromethane (CH$_2$Cl$_2$) of the compounds having formula (Ib) (MPDTTBOP) (concentration MPDTTBOP=6.21×10$^{-5}$ moles/liter), formula (Ic) (POPDTTBOP) (concentration POPDTTBOP=3.83×10$^{-5}$ moles/liter), and formula (Id) (2,4,6-(POP)$_3$DTTBOP) (concentration 2,4,6-(POP)$_3$DTTBOP=2.24×10$^{-5}$ moles/liter), prepared as reported in Examples 2, 3 and 4, respectively, were prepared.

On each solution thus obtained, the absorption spectrum, the molar extinction coefficient (ε), the emission spectrum and the Stokes shift were acquired, operating as described above: the values obtained are reported in Table 3.

Table 3 reports, in the order: the number of the example (Example), the number that refers to the formula of the compound used (Compound formula), the number of the example wherein the compound has been prepared (Prep. example), the value of the maximum of the lowest energy band in the absorption spectrum [$\lambda_{max}$ (abs.)] expressed in (nm), the molar extinction coefficient (ε) expressed in liters× moles$^{-1}$×cm$^{-1}$ (1×moles$^{-1}$×cm$^{-1}$) the value of the maximum of the highest energy band in the emission spectrum [$\lambda_{max}$ (emiss.)] expressed in (nm) and finally the value of the Stokes shift expressed in (cm$^{-1}$).

TABLE 3

| Example | Compound formula | Prep. example | $\lambda_{max}$ (abs.) (nm) | ε (1 × moles$^{-1}$ × cm$^{-1}$) | $\lambda_{max}$ (emiss.) (nm) | Stokes shift (cm$^{-1}$) |
|---|---|---|---|---|---|---|
| 9 | (Ia$_1$) | 1 | 473 | 21228 | 604 | 4585 |
| 10 | (Ib) | 2 | 486 | 29467 | 623 | 4525 |
| 11 | (Ic) | 3 | 509 | 37668 | 645 | 4142 |
| 12 | (Id) | 4 | 510 | 31615 | 668 | 4638 |

EXAMPLES 13-16

Determination of the Luminescence Quantum Efficiency (Φ) in Solution of Compounds Having General Formula (Ia)

Using the solutions prepared as reported in Examples 9-12 containing the compounds having formula (Ia$_1$) (DTTBOP), formula (Ib) (MPDTTBOP), formula (Ic) (POPDTTBOP) and formula (Id) (2,4,6-(POP)$_3$DTTBOP), prepared as reported in Examples 1, 2, 3 and 4, respectively, the luminescence quantum efficiency (Φ) was acquired, using 4,7-di-(thien-2'-yl)-2,1,3-benzothiadiazole (DTB) dissolved in anhydrous dichloromethane (CH$_2$Cl$_2$), as external standard and operating as described above.

The values obtained are reported in Table 4 which reports, in the order: the number of the example (Example), the number that refers to the formula of the compound used (Compound formula), the number of the example wherein the compound has been prepared (Prep. example) and finally the luminescence quantum efficiency (Φ) expressed as a percentage (%).

TABLE 4

| Example | Compound formula | Prep. example | Φ (%) |
|---|---|---|---|
| 13 | (Ia) | 1 | 95 |
| 14 | (Ib) | 2 | 85 |
| 15 | (Ic) | 3 | 80 |
| 16 | (Id) | 4 | 72 |

EXAMPLE 17 (COMPARATIVE)

6 g of Altuglas VSUVT 100 (PMMA) polymethylmethacrylate and 49.5 mg of 4,7-di-(thien-2'-yl)-2,1,3-benzothiadiazole (DTB), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate. The main face of the polymer plate [the one coated with the thin film containing 4,7-di-(thien-2'-yl)-2,1,3-benzothiadiazole (DTB)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 5.69 mW (FIG. 1).

Figure 2:
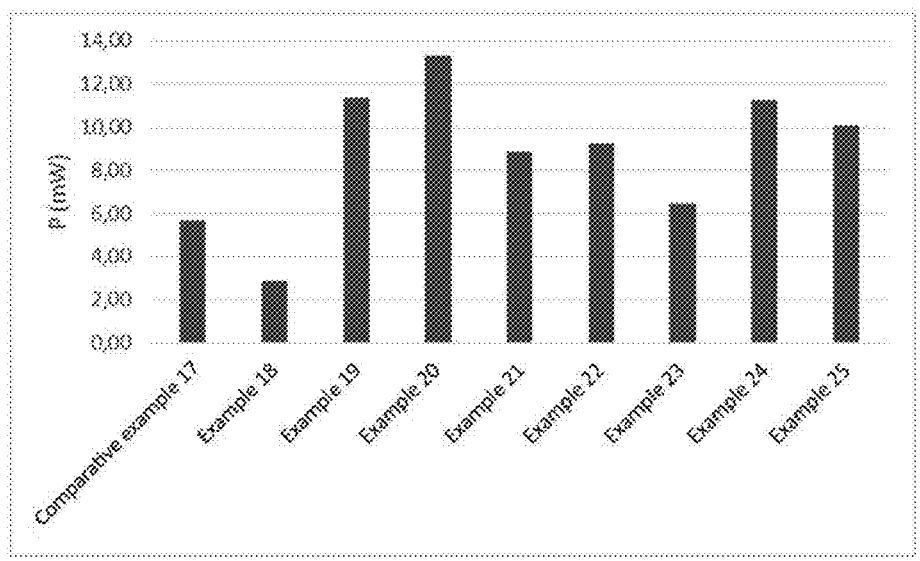
FIG. 2 shows the power value obtained.

FIG. 2 shows the power value (P) generated expressed in mW (reported on the ordinate) obtained (the number of the example is reported on the abscissa).

EXAMPLE 18 (DISCLOSURE)

6 g of Altuglas VSUVT 100 (PMMA) polymethylmethacrylate and 101.9 mg of 4,7-dithienothienyl-5,6-diphenoxy-2,1,3-benzothiadiazole having formula (Ia$_1$) (DTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-dithienothienyl-5,6-diphenoxy-2,1,3-benzothiadiazole having formula (Ia$_1$) (DTTBOP),] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 2.90 mW (FIG. 1).

FIG. 2 shows the power value (P) generated expressed in mW (reported on the ordinate) obtained (the number of the example is reported on the abscissa).

EXAMPLE 19 (DISCLOSURE)

6 g of Altuglas VSUVT 100 (PMMA) polymethylmethacrylate and 72.3 mg of 4,7-di-(2,6-dimethylphenyl)thienothienyl-5,6-diphenoxy-2,1,3-benzothiadiazole having formula (Ib) (MPDTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-di-(2,6-dimethylphenyl)thienothienyl-5,6-diphenoxy-2,1,3-benzothiadiazole having formula (Ib) (MPDTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 11.39 mW (FIG. 1).

FIG. 2 shows the power value (P) generated expressed in mW (reported on the ordinate) obtained (the number of the example is reported on the abscissa).

EXAMPLE 20 (DISCLOSURE)

6 g of Altuglas VSUVT 100 (PMMA) polymethylmethacrylate and 150.0 mg of 4,7-di-(2,6-dimethylphenyl)thienothienyl-5,6-diphenoxy-2,1,3-benzothiadiazole having formula (Ib) (MPDTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate. The main face of the polymer plate [the one coated with the thin film containing 4,7-di-(2,6-dimethylphenyl)thienothienyl-5,6-diphenoxy-2,1,3-benzothiadiazole having formula (Ib) (MPDTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 13.30 mW (FIG. 1).

FIG. 2 shows the power value (P) generated expressed in mW (reported on the ordinate) obtained (the number of the example is reported on the abscissa).

EXAMPLE 21 (DISCLOSURE)

6 g of Altuglas VSUVT 100 (PMMA) polymethylmethacrylate and 47.8 mg of 4,7-di-2-(2-phenoxyphenyl)thienothienyl-5,6-diphenoxy-2,1,3-benzothiadiazole having formula (Ic) (POPDTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-di-2-(2-phenoxyphenyl)thienothienyl-5,6-diphenoxy-2,1,3-benzothiadiazole having formula (Ic) (POPDTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 8.84 mW (FIG. 1).

FIG. 2 shows the power value (P) generated expressed in mW (reported on the ordinate) obtained (the number of the example is reported on the abscissa).

EXAMPLE 22 (DISCLOSURE)

6 g of Altuglas VSUVT 100 (PMMA) polymethylmethacrylate and 86.1 mg of 4,7-di-2-(2-phenoxyphenyl)thienothienyl-5,6-diphenoxy-2,1,3-benzothiadiazole having formula (Ic) (POPDTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-di-2-(2-phenoxyphenyl)thienothienyl-5,6-diphenoxy-2,1,3-benzothiadiazole having formula (Ic) (POPDTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 9.25 mW (FIG. 1).

FIG. 2 shows the power value (P) generated expressed in mW (reported on the ordinate) obtained (the number of the example is reported on the abscissa).

EXAMPLE 23 (DISCLOSURE)

6 g of Altuglas VSUVT 100 (PMMA) polymethylmethacrylate and 172.2 mg of 4,7-di-2-(2-phenoxyphenyl)thienothienyl-5,6-diphenoxy-2,1,3-benzothiadiazole having formula (Ic) (POPDTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-di-2-(2-phenoxyphenyl)

thienothienyl-5,6-diphenoxy-2,1,3-benzothiadiazole having formula (Ic) (POPDTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 6.84 mW (FIG. 1).

FIG. 2 shows the power value (P) generated expressed in mW (reported on the ordinate) obtained (the number of the example is reported on the abscissa).

EXAMPLE 24 (DISCLOSURE)

6 g of Altuglas VSUVT 100 (PMMA) polymethylmethacrylate and 241.0 mg of 4,7-di-2-(2,4,6-triphenoxyphenyl) thienothienyl-5,6-diphenoxy-2,1,3-benzothiadiazole having formula (Id) (2,4,6-(POP)$_3$DTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-di-2-(2,4,6-triphenoxyphenyl) thienothienyl-5,6-diphenoxy-2,1,3-benzothiadiazole having formula (Id) (2,4,6-(POP)$_3$DTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 11.25 mW (FIG. 1).

FIG. 2 shows the power value (P) generated expressed in mW (reported on the ordinate) obtained (the number of the example is reported on the abscissa).

EXAMPLE 25 (DISCLOSURE)

6 g of Altuglas VSUVT 100 (PMMA) polymethylmethacrylate and 158.0 mg of 4,7-di-2-(2,4,6-triphenoxyphenyl) thienothienyl-5,6-diphenoxy-2,1,3-benzothiadiazole having formula (Id) (2,4,6-(POP)$_3$DTTBOP), were dissolved in 30 ml of 1,2-dichlorobenzene (Aldrich). The obtained solution was subsequently deposited, evenly, on a polymethylmethacrylate plate (dimensions 300 mm×90 mm×6 mm) using a "Doctor Blade" type film applicator and the solvent was allowed to evaporate at room temperature (25° C.), in a light air flow, for 24 hours. The result was a transparent plate in yellow conferred by the film whose thickness was found to be comprised between 100 μm and 50 μm.

An IXYS-KXOB22-12 photovoltaic cell having a 1.2 cm$^2$ surface was then applied to one of the edges of the polymer plate.

The main face of the polymer plate [the one coated with the thin film containing 4,7-di-2-(2,4,6-triphenoxyphenyl) thienothienyl-5,6-diphenoxy-2,1,3-benzothiadiazole having formula (Id) (2,4,6-(POP)$_3$DTTBOP)] was then lit up with a light source with a power equal to 1 sun (1000 W/m$^2$) and the electrical power generated by the effect of lighting was measured.

The power measurements (P) were made by illuminating a portion of a plate with dimensions equal to 100 mm×90 mm, at an increasing distance (d) from the edge on which the photovoltaic cell was fixed. These measurements at a variable distance from the photovoltaic cell allow the contribution of wave guide, edge, diffusion and self-absorption effects to be quantified.

FIG. 1 shows the curve relating to the generated power value (P) expressed in mW (reported on the ordinate), as a function of the distance (d) from the edge on which the photovoltaic cell was fixed, expressed in cm (reported on the abscissa).

It can be seen how, in the absence of edge effects, the average power generated is equal to 10.08 mW (FIG. 1).

FIG. 2 shows the power value (P) generated expressed in mW (reported on the ordinate) obtained (the number of the example is reported on the abscissa).

The invention claimed is:

1. The diaryloxybenzoheterodiazole compound disubstituted with thienothiophenic groups having general formula (Ia):

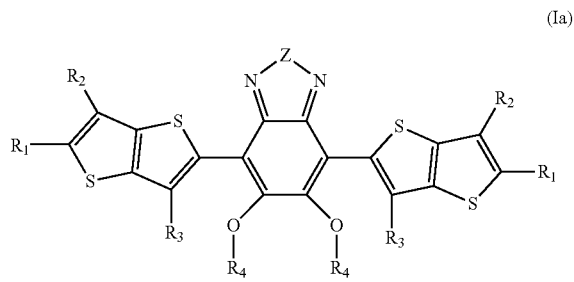

wherein
Z represents a sulphur atom, an oxygen atom, a selenium atom; or an NR$_5$ group wherein R$_5$ is selected from C$_1$-C$_{20}$ alkyl groups, preferably C$_1$-C$_8$, linear or branched, or from optionally substituted aryl groups;
R$_1$, R$_2$ and R$_3$, equal to or different from each other, represent a hydrogen atom; or are selected from C$_1$-C$_{20}$ alkyl groups, preferably C$_1$-C$_8$, linear or branched, optionally containing heteroatoms, optionally substituted cycloalkyl groups, optionally substituted aryl groups, C$_1$-C$_{20}$ alkoxy groups, preferably C$_1$-C$_8$, linear or branched, optionally substituted, —COOR$_6$ groups wherein R1 is selected from $C_1$-$C_{20}$ alkyl groups, preferably $C_1$-$C_8$, linear or branched, or is a cyano group;

or $R_1$ and $R_2$, may optionally be bound together so as to form, together with the carbon atoms to which they are bound, a saturated, unsaturated, or aromatic cycle or a polycyclic system containing from 3 to 14 carbon atoms, preferably from 4 to 6 carbon atoms, optionally containing one or more heteroatoms such as oxygen, sulfur, nitrogen, silicon, phosphorus, selenium;

$N_4$, equal to or different from each other, are selected from optionally substituted aryl groups.

2. The diaryloxybenzoheterodiazole compound di-substituted with thienothiophenic groups according to claim 1, wherein in said general formula (Ia):

Z represents a sulphur atom;

$R_1$, equal to each other, represent a hydrogen atom; or are selected from optionally substituted aryl groups, preferably are 2,6-dimethylphenyl, 2-phenoxyphenyl, 2,4,6-triphenoxyphenyl;

$R_2$ and $R_3$, equal to each other, represent a hydrogen atom;

$R_4$ is selected from optionally substituted aryl groups, preferably is phenyl.

3. A luminescent solar concentrator (LSC) including at least one diaryloxylbenzoheterodiazole compound di-substituted with thienothiophenic groups having a general formula (Ia) according to claim 1 or 2.

4. A photovoltaic device or solar device comprising at least one photovoltaic cell or solar cell, and at least one luminescent solar concentrator (LSC) according to claim 3.

5. Use of a photovoltaic device or solar device according to claim 4 in the construction of greenhouses.

6. The diaryloxybenzoheterodiazole compound di-substituted with thienothiophenic groups according to claim 1, wherein the $C_1$-$C_{20}$ alkyl groups of $R_5$ are selected from $C_1$-$C_8$ alkyl groups.

7. The diaryloxybenzoheterodiazole compound di-substituted with thienothiophenic groups according to claim 1, wherein the $C_1$-$C_2$ alkyl groups of $R_1$, $R_2$ or R3, are selected from $C_1$-$C_8$ alkyl groups.

8. The diaryloxybenzoheterodiazole compound di-substituted with thienothiophenic groups according to claim 1, wherein the $C_1$-$C_2$ alkyl groups of $R_6$ are selected from $C_1$-$C_8$ alkyl groups.

9. The diaryloxybenzoheterodiazole compound di-substituted with thienothiophenic groups according to claim 1, wherein the aromatic cycle or polycyclic system.

10. The diaryloxybenzoheterodiazole compound di-substituted with thienothiophenic groups according to claim 1, wherein the one or more heteroatoms of $R_1$ and $R_2$ are selected from the group consisting of oxygen, sulfur, nitrogen, silicon, phosphorus, and selenium.

11. The diaryloxybenzoheterodiazole compound di-substituted with thienothiophenic groups according to claim 2, wherein the optionally substituted aryl groups of $R_1$ are selected from the group consisting of 2,6-dimethylphenyl, 2-phenoxyphenyl, and 2,4,6-triphenoxyphenyl.

12. The diaryloxybenzoheterodiazole compound di-substituted with thienothiophenic groups according to claim 2, wherein the optionally substituted aryl groups of R4 are phenyl.

* * * * *